United States Patent [19]

Tenud et al.

[11] Patent Number: 4,670,192

[45] Date of Patent: Jun. 2, 1987

[54] OPTICALLY-ACTIVE DI-[3-CHLORO-2-OXY-PROPYLTRIME-THYLAMMONIUM]-TARTRATE

[75] Inventors: Leander Tenud, Visp; Jacques Gosteli, Basel, both of Switzerland

[73] Assignee: Lonza Ltd., Gampel/Valais, Switzerland

[21] Appl. No.: 877,785

[22] Filed: Jun. 24, 1986

Related U.S. Application Data

[60] Division of Ser. No. 832,760, Feb. 25, 1986, which is a continuation-in-part of Ser. No. 717,547, Mar. 29, 1985.

[30] Foreign Application Priority Data

Apr. 4, 1985 [CH] Switzerland .................. 1704/84

[51] Int. Cl.⁴ ............................................. C07C 95/00
[52] U.S. Cl. .................................................. 260/501.15
[58] Field of Search .................................... 260/501.15

[56] References Cited

U.S. PATENT DOCUMENTS

| | | | |
|---|---|---|---|
| 2,303,602 | 12/1942 | Braun | 260/536 |
| 2,692,285 | 10/1954 | Robinson | 260/567.6 |
| 3,135,788 | 6/1964 | Noguchi et al. | 260/531 |
| 3,151,149 | 9/1964 | Strack et al. | 260/465.5 |
| 3,488,379 | 1/1970 | Dohi et al. | 260/465.4 |
| 4,070,394 | 1/1978 | Wiegand | 260/465.5 |

FOREIGN PATENT DOCUMENTS

| | | |
|---|---|---|
| 660039 | 2/1965 | Belgium . |
| 23217 | 5/1962 | German Democratic Rep. . |
| 752681 | 7/1956 | United Kingdom . |

*Primary Examiner*—Paul J. Killos
*Attorney, Agent, or Firm*—Fisher, Christen & Sabol

[57] ABSTRACT

Process for the production of optically-active di-[3-chloro-2-hydroxy-propyltrimethylammonium]-tartrate. Racemic 3-chloro-2-hydroxy-propyltrimethylammonium-chloride is converted by racemate resolution with optically-active tartaric acid into the optically-active di-[3-chloro-2-hydroxy-propyltrimethylammonium]-tartrate. Such optically-active tartrate compound is dissociated in tartaric acid and optically-active 3-chloro-2-hydroxy-propyltrimethylammonium-chloride and the latter is converted with inorganic cyanides. From the product, the production of optically-active carnitine nitrile chloride can be achieved.

3 Claims, No Drawings

OPTICALLY-ACTIVE DI-[3-CHLORO-2-OXY-PROPYLTRIMETHYLAM-MONIUM]-TARTRATE

This is a divisional application of application Ser. No. 832,760, filed on Feb. 25, 1986, which is a continuation-in-part of application Ser. No. 717,547, filed on Mar. 29, 1985.

BACKGROUND OF THE INVENTION

1. Field of the Invention

This invention relates to optically-active tartrate compounds, to methods of making such optically-active tartrate compounds and to the use of such optically-active tartrate compounds for the production of optically-active conversion products.

2. Prior Art

Due to the slight stability of the free group of acids, the racemic resolution of free carnitine causes difficulties; so the nitrile or the amides of carnitine are predominantly used for its racemic separation. For example, East German Pat. No. 23,217 teaches converting carnitine nitrile chloride, which has been converted by treatment with silver oxide into the hydroxide or by treatment with silver carbonate into the carbonate, with an optically-active acid into the diastereomers from which the suitable diastereomer is separated. The desired carnitine derivative is isolated from the suitable diastereomer. Another path, taught by Belgian Pat. No. 660,039, starts out from carnitine amide hydrochloride, which is converted with camphoric acid in the presence of $AgNO_3$ into the diastereomeric mixture. The suitable diastereomer is again separated and analyzed.

However, the above processes have considerable disadvantages. Among such disadvantages is the difficultly-separable salt impurities obtained in large quantities, which make the dissociation of the racemate difficult. Also the numerous steps of the processes which are required to provide the carnitine amides, respectively, carnitine nitriles, accessible for the racemate dissociation make a technical or commercial application too expensive with regard to costs. These difficulties are increased, since as a result of the use of silver salts, one must operate with the exclusion of light in order to avoid any blackening of the reaction material.

BROAD DESCRIPTION OF THE INVENTION

An object of the invention is to provide the new compound di-[3-chloro-2-hydroxy-propyltrimethylammonium]-tartrate. Another object of the invention is to provide the new compound di-[(−)-3-chloro-2-hydroxy-propyltrimethylammonium]-L-(+)-tartrate (sometimes herein termed COP-tartrate). A further object of the invention is to provide a process for the production of such new compounds. A still further object of the invention is to provide a method for the production of optically-active carnitine nitrile chloride from such new compounds. Another object of the invention is to provide a process which eliminates the above-described disadvantages of the prior art. Another object of the invention is to provide a process which produces, in a simple manner, optically-active carnitine nitrile chloride, especially (−)-carnitine nitrile chloride. Other objects and advantage of the invention are set out herein or are obvious herefrom to one skilled in the art.

The advantages and objects of the invention are achieved by the compounds and processes of the invention.

The invention includes optically-active di-[3-chloro-2-hydroxy-propyltrimethylammonium]-tartrate. For the production of (−)-carnitine nitrile chloride, one uses di-[(−)-3-chloro-2-hydroxy-propyltrimethylammonium]-L-(+)-tartrate (COP tartrate).

The new optically-active di-[3-chloro-2-hydroxy-proyltrimethylammonium]-tartrate has the formula:

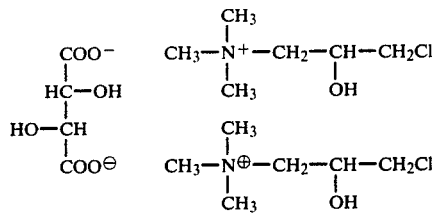

The inventio also includes:
(a) di[(−)-3-chloro-2-hydroxy-propyltrimethylammonium]-L-(+)-tartrate; and
(b) di[(+)-3-chloro-2-hydroxy-propyltrimethylammonium]-D-(−)-tartrate.

The invention also involves producing the COP-tartrate. The COP-tartrate can be produced by several different methods. Preferably, the COP-tratrate is produced either by conversion of racemic 3-chloro-2-hyroxy-propyltrimethylammonium-chloride with L-(+)-tartaric acid, effectively in the presence of a trialkylamine, or by conversion of L-(+)-tartaric acid with trimethylamine and subsequent conversion with epichlorohydrin. When proceeding according to the first method, first the racemic 3-chloro-2-hydroxy-propyltrimethylammonium-chloride is produced from epichlorohydrin and trimethylamine and then the racemic 3-chloro-2-hydroxy-propyltrimethylammonium-chloride is converted with L-(+)-tartaric acid in the presence of a trialkylamines into the COP-tartrate.

The COP-tartrate can be dissociated from its diastereomer by crystallization.

The trialkylamine is preferably a trialkylamine wherein each of the alkyl groups has 2 to 12 carbon atoms. While the trialkylamine can have branched alkyl groups, preferably the trialkylamine only has straight-chain alkyl groups. Examples of the preferred trialkylamines are triethylamine, tributylamine, tripropylamine, tripentylamine and trioctylamine. Most preferably tri-butylamine is used.

A preferred embodiment for the production of the COP-tartrate according to the invention is described as follows: Starting out from 1 mole of dextrogyric tartaric acid, effectively 1.6 to 3 moles, preferably 1.8 to 2.5 moles, of tri-n-butylamine are converted with effectively 1.6 to 3 moles, preferably 1.8 to 2.2 moles, of racemic 3-chloro-2-hydroxy-propyltrimethylammonium-chloride for the production of the diastereomeric mixture. Preferably the conversion is operated in the presence of water and/or a solvent which is not miscible with water, such as, methylene chloride or chloroform, and at a temperature of 0° to 30° C., preferably 15° to 25° C. After separation of the tri-n-alkylamine hydrochloride by extraction with an inert solvent, such as, methylene chloride or chloroform, the desired isomer is isolated by fractional crystallization after evaporation of the aqueous phase under reduced pressure. Effectively, the diastereomeric mixture is dissolved in a solvent, for example, water or a lower alkanol, such as, ethanol or preferably methanol. The crystallization of the desired isomer of the COP-tartrate is effectively achieved by the addition of a diluent, preferably acetone.

According to another production method of the invention L-(+)-tartaric acid dissolved in water or suspended in an alcohol (lower alkanol), effectively methanol or ethanol, is placed in a vessel, subsequently neutralized with trimethylamine, and then the di-[trimethylammonium]-tartrate formed as an intermediate product is converted with epichlorohydrin at a temperature of 17° to 30° C. into the desired COP-tartrate and its diastereomers.

A preferred embodiment for the production of the COP-tartrate according to the invention is as follows: Starting out with 1 mole of L-(+)-tartaric acid, dissolved in 200 to 250 g of water or suspended in a lower (alkanol) alcohol, 1.6 to 2.5 moles, preferably 1.8 to 2.1 moles, of trimethylamine is added at a temperature of 0° to 30° C. The pH of the solution effectively is 6.5 to 7.5. Subsequently and effectively, 1.6 to 3 moles of epichlorohydrin is added and the temperature is held at 15° to 30° C., preferably 20° to 28° C.

Whenever the invention is operated with water, one aqueous phase develops. After evaporation of the water, effectively under vacuum, an oily residue results from which by treatment with organic solvent(s), effectively with methanol/acetone, the desired COP-tartrate is crystallized out. Whenever one operates with alcohols (e.g., lower alkanol, such as methanol or ethanol), then the desired COP-tartrate is precipitated and can be separated.

A further method for the production of COP-tartrate is where first the silver salt of the tartaric acid is produced from silver nitrate and alkali tartrate. Then the silver tartrate is suspended in water and is converted with racemic 3-chloro-2-hydroxy-propyltrimethylammonium-chloride. The desired COP-tartrate can be obtained by crystallization or can be separated from the diastereomeric salt.

The di-[(−)-3-chloro-2-hydroxy-propyltrimethylammonium]-L-(+)-tartrate of the invention has the following properties and characteristics:

Melting point of 159° C. (after recrystallization from methanol/acetone) $[\alpha]_D^{24} = -10.8°$ (c=1.04 in water) pH of the solution (1 percent) is 7

Analysis: C, calculated is 42.39%, found is 42.36% H, calculated is 7.56%, found is 7.99% N, calculated is 6.18%, found is 6.36%

IR (KBr) spectrum: 3.5, 6.30, 7.20, 9.15, 10.25 micron.

For the production of di[(+)-3-chloro-2-hydroxy-propyltrimethylammonium]-D-(−)-tartrate, the racemate dissociation is conducted using D-(−)-tartaric acid. Such product has the following properties and characteristics:

Melting point 159° C. (after recrystallization from methanol/acetone). $[\alpha]_D^{24} = +10.8°$ (c=1.04 in water).

As a result of the process of the invention, the racemate dissociation takes place very early in such production schemes. Thus one can work starting with the further steps up to the carnitine nitrile chloride and carnitine still with only one antipode, as a result of which the load of the further reactions by the other antipode is omitted. One ordinarily skilled in the art could not anticipate that no further racemization would occur in the case of a subsequent reaction which in the end leads to the carnitine.

The di-[(−)-3-chloro-2-hydroxy-propyltrimethylammonium-L-(+)-tartrate (COP tartrate) can be converted in a simple manner into the (−)-carnitine nitrile chloride and (−)-carnitine. At the same time, one can convert the COP-tartrate first of all with $CaCl_2$, followed by separating the Ca-tartrate and isolating the (−)-3-chloro-2-hydroxy-propyltrimethylammonium-chloride. The $CaCl_2$ can be replaced with, for example, 2 equivalents of HCl (aqueous) and 1 equivalent of KDH (aqueous) or 1 equivalent of HCl (aqueous) and 1 equivalent KCl (aqueous). The latter can be converted using an alkali cyanide into the (−)-carnitine nitrile chloride. The alkali cyanide is, for example, LiCN or KCN, but preferably is NaCN. However, one can also carry out the decomposition, i.e., double salt conversion, of the COP-tartrate and the cyanide substitution reaction in one step. In that case, effectively an alkaline earth cyanide, preferably $Ca(CN)_2$ is used. At the same time the tartaric acid precipitates as the Ca-salt and the (−)-carnitine nitrile chloride can be isolated from the reaction solution. No matter which method is used, the setting free or reaction is carried out preferably in water as a solvent.

According to another method of the invention, the optically active 3-chloro-2-hydroxy-propyltrimethylammonium-chloride isolated from the dissociation of the COP-tartrate is converted by treatment with a strong base, such as, an alkali hydroxide, an alkali alcoholate or an alkali tert.-butylate, into the (−)-glycidyltrimethylammonium-chloride and the latter is converted by treatment with acetone cyanohydrin or prussic acid into the L-carnitine nitrile chloride. This method is carried out preferably in an alcohol (lower alkanol) as a solvent at a temperature around ambient temperature.

The purification of the product can be achieved effectively by simple crystallization from a solvent, such as, a lower (alkanol) alcohol. Thus, products with optical purities of 98 plus are obtained.

However, according to this process, the di-[(+)-3-chloro-2-hydroxy-propyltrimethylammonium]-D-(−)-tartrate can also be converted into the corresponding (+)-carnitine nitrile chloride.

DETAILED DESCRIPTION OF THE INVENTION

As used herein, all parts, percentages, ratios and proportions are on a weight basis unless otherwise stated herein or otherwise obvious herefrom to one skilled in the art.

EXAMPLE 1

Production Of Di-[3-chloro-2-hydroxy-propyltrimethylammonium]-tartrate

While stirring, 18.54 g (100 mmole) of tri-n-butylamine was added drop by drop to 7.50 g (50 mmole) of L-(+)-tartaric acid, which was dissolved in 50 ml of water, whereby the solution was heated to 30° C. Subsequently, 18.81 g (100 mmole) of 3-chloro-2-hydroxy-propyltrimethylammonium chloride, which was dissolved in 100 ml of water, was added to the solution. The resultant clear solution was extracted with 8 separate portions of 150 ml of methylene chloride. The extractions were evaporated under vacuum. 21.65 g (97.6 percent yield) of tributylamine hydrochloride was obtained. (Together, the two last extractions only still contained 0.14 g of material.) The aqueous layer was evaporated in a rotary evaporator until dry. 23.22 g of a very viscous oil (102.5 percent) resulted. This was dissolved hot in 30 ml of methanol. It was mixed slowly with 93 ml of acetone until it became cloudy. The latter was again made to disappear by the addition of a few drops of methanol. After 72 hours, the mother liquor was decanted. The crystal crust was washed with acetone/methanol (3:1) and was dried under vacuum. The yield was 7.20 g of crystals (31.8 percent or 63.6 percent of the theory). The crystals had a melting point of 147° to 170° C. The crude tartrate was dissolved in 10 g of hot methanol and gradually 45 ml of acetone were added, whereupon the crystallization immediately started. The crystallization vessel was kept overnight in the refrigerator. The mother liquor was decanted off; the crystal cake was washed with acetone and dried. 5.78 g of crystals, corresponding to 51 percent of the theory, were obtained. The crystals had a melting point of 150° to 152° C. and a $[\alpha]_D^{24}$ of $-7.5°$ (c=1.04 in water). The tributylamine was recovered from the methylene chloride residue (raw tributylamine hydrochloride) with a yield of 96 percent by placing the residue in a solution of methylene chloride, shaking the solution with 1N of caustic soda solution and removing the solvent under vacuum.

EXAMPLE 2

Production Of
Di-[(−)-3-chloro-2-hydroxy-propyltrimethylammonium]-L-(+)-tartrate To 18.75 g (125 mmole) of L-(+)-tartaric acid, which was dissolved in 30 ml of water, 39 ml (259 mmole) of trimethylamine was added dropwise within 10 minutes while stirring. The temperature was kept at 30° C. The pH of the solution was 7. Subsequently, the solution was cooled to 15° C. and 23.15 g (250 mmole) of epichlorohydrin was added dropwise while stirring. The reaction temperature was kept at 25° C. and the stirring was continued until the mixture consisted only of a liquid phase. After completing the reaction, the water was evaporated under vacuum (Rotavap) at 40° C. 59.5 g of a viscous oil resulted. This residue was dissolved in 40 ml of hot methanol and gradually 135 ml of acetone were added until cloudiness occurred. After letting the solution stand for 72 hours, at ambient temperature, the mother liquor was decanted off and the crystals were washed with acetone/methanol (4:1) and dried under vacuum. 4.75 g of plate-shaped crystals resulted. The yield of crystals was 16.8 percent of the theory. The crystals had a melting point of 150° to 152° C. and a $[\alpha]_D^{24}$ of $-8.1°$ (c=1 in water).

EXAMPLE 3

Production Of
Di-[(−)-3-chloro-2-hydroxy-propyltrimethylammonium]-L-(+)-tartrate 150 g (1 mmole) of L-(+)-tartaric acid was suspended in 200 g of methanol and, at a temperature of 20° C., 106.2 g (1.8 mole) of trimethylamine and 250 g of ethanol were added within 1 hour. The temperature was kept at 20° C. The tartaric acid was dissolved while forming di-trimethylammonium-L-(+)-tartrate. Subsequently, 166.5 g (1.8 mole) of epichlorohydrin was added and the temperature was kept at 20° C. The stirring continued for 2 days while maintaining such temperature. The emerging crystals were filtered off, washed with acetone/methanol (4:1) and dried under vacuum. The product was obtained in a yield of 38.9 percent (77.8 percent of the theory). The product had a melting point of 157° to 158° C. and had a $[\alpha]_D^{24}$ of $-9.1°$ (c=1 in water).

EXAMPLE 4

Production Of
Di-[(−)-3-chloro-2-hydroxy-propyltrimethylammonium]-D-(−)-tartrate 46.25 g (127 mmole) of di-silver-L-(+)-tartrate was suspended in 350 ml of water and was mixed with a solution of 3-chloro-2-hydroxy-propyltrimethylammonium chloride, which was dissolved in water. The suspension was stirred for 4 hours. The silver chloride formed was filtered off and (for the purpose of quick drying) was washed with methanol and ether and then dried. 36.21 g of silver chloride (99.5 percent of the theory) resulted. The filtrate was completely evaporated in a rotary evaporator. The residue weighed 61.43 g (theory: 57.58 g) after drying in an oil vacuum (5 hours at room temperature). The crystal cake was dissolved in 80 ml of hot methanol and 260 ml of acetone was added gradually to the hot solution. The turbidity which developed was made to disappear by the addition of 2 ml of methanol. The vessel was closed and allowed to cool. After a few minutes, crystallization started at the wall of the vessel. After 48 hours, the vessel and its contents were still kept for 3 hours in a refrigerator (+4° C.). The mother liquor was decanted from the crystal crust. The crystals were washed with approximately 20 ml of acetone/methanol (1:5) and a little acetone, and were then dried under vacuum. 19.33 g of crystal clusters resulted which had a melting point o 159° C. (after crystallization from acetone/methanol) and a $[\alpha]_D^{24}$ of $+10.8°$ (c=1.04 in water).

EXAMPLE 5

Production Of
(−)-3-chloro-2-hydroxy-propyltrimethylammonium-chloride 4.50 g (40.5 mmole) of calcium chloride, which was dissolved in 15 ml of water, was added dropwise to 18.35 g of (40.5 mmole) of tartrate (according to Example 1), which was dissolved in 65 ml of water while rotating the vessel. The calcium tartrate immediately crystallically precipitated. After 5 minutes, the suspension was cooled in an ice bath (the solution had a pH of 7) and the calcium tartrate was filtered off. After washing with methanol and drying in air, the material weighed 10.08 g (theory for the tetrahydrate: 10.54 g, yield 95.6 percent). The filtrate (and wash-methanol) was evaporated at a 50° C. bath temperature in a rotary evaporator. The solid residue, which weighed 17.0 g (theory: 15.24 g), was digested at 70° C. with 25 ml of absolute ethanol. The suspension was cooled in an ice bath and the crystals were filtered. After washing with ethanol/acetone (1:1) and acetone, the material was dried in air. The yield was 10.24 g of colorless crystals (67.2 percent of the theory). The colorless crystals had a melting point of 214° C. and a $[\alpha]_D^{24}$ of $-28.76°$ (c=0.97 in water).

EXAMPLE 6

Production of (−)-carnitine nitrile chloride 8.61 g (45.76 mmole) of the product produced according to Example 5 in 9 ml of methanol and 1 ml of water was mixed dropwise in a bath (50° to 55° C.) within 3 minutes with 3.43 g (47.0 mmole) of sodium cyanide in 8 ml of water. The reaction solution, which immediately became turbid, was left in the bath for 20 minutes (pH 8 to 9) and was then adjusted to pH 5 with 5.5N hydrochloric acid (3.0 ml of acid was needed). After cooling of the composition with a bath (−100° C.) for a few minutes, the melt obtained was filtered off, washed with ice-cold methanol and dried. 1.89 g of salt was obtained. The filtrate was concentrated under vacuum at a 40° C. bath temperature. The residue, a yellowish solid mass (10.6 g), was taken in 23 g of hot methanol. The warm solution (40° C.) was filtered (removal of 0.60 g of insoluble material). The filtrate was again filtered (separation of about 0.1 g of salt), heated until settling (weight of the solution, 24 g) and cooled to 0° C. The separated crystals were subjected to suction, washed with a little methanol (−10° C.) and ether, and dried. The yield was 4.62 g of almost colorless crystals (56.5 percent of the theory). The crystals had a melting point of 244° C. and a $[\alpha]_D^{24}$ of −28.30° (c=1.06 in water). The product contained starting material (tlc). After being twice recrystallized from ethanol (95 percent), long needles were obtained which had a melting point of 256° C. and a $[\alpha]_D^{24}$ of −25.9° (c=1.05 in water).

EXAMPLE 7

Production of (−)-glycidyltrimethylammoniumchloride ((−)-N,N,N-trimethyl-oxiranemethane amine)

At ambient temperature while stirring, a solution of 2.05 g NaOH (98 percent 50 mmole) in 45 ml of methanol was added dropwise to 9.5 g (50 mmole) of (−)-3-chloro-2-hydroxy-trimethylammonium-chloride [99.1 percent $[\alpha]_D^{24}$= −29.5° (c=1, H$_2$O), melting point 212° to 214° C.] dissolved in 35 ml of methanol. The mixture was stirred for 3 hours. The precipitated NaCl (2.6 g, 89 percent was filtered off and washed twice with portions of 5 ml of ethanol. The filtrate and the wash ethanol were evaporated. The raw product (8.95 g, 117 percent) was absorbed in 50 ml of chloroform, whereupon, after shaking, the product gradually dissolved except for some NaCl. This insoluble NaCl (0.60 g, 20 percent) was filtered off. After evaporating off the CHCl$_3$, 7.6 g (99.3 percent) (−)-glycidyltrimethylammoniumchloride was obtained. The product did not contain any starting material (tlc). The product had a melting point of 121° to 123.5° C. and a $[\alpha]_D^{24}$ of −27.0° (c=1 in water). Analysis of the product showed:

IR (KBr): 3440s, 3030w, 2980w, 2940w, 1630w, 1485s, 1420w, 1270w, 1150w, 1100w, 980m, 935s, 900m, 870m 805w 770w $^1$H-NMR (300 MHz, d$_6$-DMSO): 2,69 (dd, 1H, J=5 and 3 Hz, H-C(3)); 2,93 (dd, 1H, J=5 and 5 Hz, H-C(3)); 3,22 (dd, 1H, J=13 and 8 Hz, H-C(1)); 3,23 (s, 9H, —N(CH$_3$)$_3$); 3,57 (dddd, 1H, J=8/5/3 and 3 Hz, H-C(2)); 4,04 (dd, 1H, J=13 and 3 Hz, H-C(1)).

EXAMPLE 8

Production Of (−)-glycidyltrimethylammonium-chloride ((n)-N,N,N-trimethyl-oxirane methane amine At ambient temperature while stirring, a solution of 5.8 g KOtBu (97 percent, 50 mmole) in 20 ml of methanol was added dropwise to 9.5 g (50 mmole) of (−)-3-chloro-2-oxypropyltrimethylammonium-chloride [99.1 percent $[\alpha]_D^{24}$= −29.5° (c=1, in water), melting point of 212° to 214° C.], which was dissolved in 35 ml of methanol. The mixture was stirred for 3 hours. The precipitated KCl (3.95 g, 105 percent was filtered off and washed twice with portions of 5 ml of ethanol. The filtrate and the wash-ethanol were evaporated. The raw product (9.15 g, 119 percent) was taken in 50 ml of chloroform, whereupon, after shaking, the product gradually dissolved except for some KCl. This insoluble KCl (0.05 g, traces) was filtered off. After evaporating off the CHCl$_3$, 7.5 g (98 percent) (−)-glycidyltrimethylammonium-chloride was obtained. The product did not contain any starting material (tlc). The product had a melting point of 119° to 121° C. and a $[\alpha]_D^{24}$ of −27.1° (c=1 in water).

EXAMPLE 9

Production Of L-carnitine Nitrile Chloride 4.35 g of acetone cyanhydrin (98 percent, 50 mmole) and 7.9 g (50 mmole) of (−)-glycidyltrimethylammonium-chloride were added to 10 ml of MeOH (i.e., methanol). The mixture was stirred at 20° to 25° C. until all of its solid components were dissolved. After that the solution was heated within half hour to 45° C. and stirring at this temperature was continued for 4 hours (thin layer chromatogram). The product began to precipitate after one half hour at 50° C. The mixture was cooled to 20° C. The resultant white crystals were filtered, washed three times, each time with 6 ml of acetone, and dried. The yield was 7.5 g (81.6 percent of the theory) of such white crystals. The white crystals had a melting point of 246° C. (composition) and a $[\alpha]_D^{24}$ of −25.6° (c=1 in water). The product was 97.3 percent (HPLC) and contained 2.4 percent of (−)-glycidyltrimethylammonium-chloride. After recrystallization from ethanol (95 percent), long needles were obtained. The long needles had a melting point of 256° C. (decomposition) and a $[\alpha]_D^{24}$ of −25.8° (c=1 in water).

EXAMPLE 10

Production Of (−)-3-chloro-2-hydroxypropyltrimethylammonium chloride 228.3 g (0.5 mol) of di[(−)-3-chloro-2-hydroxypropyltrimethylammonium]-L-(+)tartrate was dissolved in a mixture of 315 ml of H$_2$O and 135 ml of ethanol at room temperature. Within a 2-minute period, 38.2 g (0.5 mol) of solid KCl was added to the stirred solution. The KCl dissolved within 2 to 3 minutes. 49.4 g of HCl (37 percent in H$_2$O; 0.5 mol) was added dropwise to the solution within 10 minutes. During this addition, the K,H-tartrate precipitated and the pH dropped to 3.2. The reaction mixture was stirred for 1 hour at room temperature, cooled to 4° C. and the K,H-tartrate was filtered by means of suction, washed with alcohol/water and air dried. The yield was 94.2 g [100.1 percent, $[\alpha]_D^{20}$=31.5° (c=1.1M NaOH)]. The filtrate (and wash solvent) was evaporated in a rotary evaporator at a bath temperature of 50° C. until the (−)-3-chloro-2-hydroxy-propyltrimethylammonium chloride began to precipitate. Then the mixture was cooled to room temperature. The crystals of (−)-3-chloro-2-hydroxy-propyltrimethylammonium chloride were filtered by suction, washed with ethanol/acetone and dried. The yield was 88.5 g [(47.0 percent, $[\alpha]_D^{24} = -29.7°$ (c=1, H$_2$O)]. The mother liquor and the wash solvent were evaporated to dryness. The residue was digested with 160 ml of absolute ethanol at 70° C. The suspension was cooled in an ice bath. The crystals of (−)-3-chloro-2-hydroxy-propyltrimethylammonium chloride were filtered by means of suction, washed with ethanol/acetone and dried. The yield was 83.6 g [44.5 percent, $[\alpha]_D^{24} = 29.3°$ (c=1, H$_2$O)].

EXAMPLE 11

Production Of (−)-3-chloro-2-hydroxy-propyltrimethylammonium chloride 228.3 g (0.5 mol) of di-[(−)-3chloro-2-hydroxy-propyltrimethylammonium]-L-(+)tartrate was dissolved in a mixture of 315 ml of H$_2$O and 135 ml of ethanol at room temperature. 88.9 g of HCl (37 percent in H$_2$O; 0.9 mol) was added dropwise to the stirred mixture within 8 minutes and then a solution of 28.1 g of KOH (0.5 mol) was added dropwise in 30 ml of H$_2$O within 10 minutes. the K,H-tartrate immediately precipitated crystalline. The pH was brought to 3.2 to 3.5 with 9.8 g HCl (37 percent in H$_2$O; 0.1 mol). The reaction mixture was stirred for 1 hour at room temperature, cooled to 4° C., and the K,H-tartrate was filtered by means of suction, washed with ethanol/H$_2$O and air dried. The yield was 94.6 g [100.8 percent, $[\alpha]_D^{20} = +31.3°$ (c=1.1M NaOH)]. The (−)-3-chloro-2-hydroxy-propyltrimethylammonium chloride was isolated as in Example 1.

EXAMPLE 12

Production Of (−)-3-chloro-2-hydroxy-propyltrimethylammonium chloride

The K,H-tartrate was prepared and filtered from 228.3 g (0.5 mol) of di-[(−)-3-chloro-2-hydroxy-propyltrimethylammonium]-L-(+)-tartrate according to Example 10. Then the filtrate and the wash solvent were evaporated in a rotary evaporator to a weight of 350 g. 600 ml of toluene was added and the residual water was distilled off azeotropically. After distillation of about 150 g of water, the (−)-3-chloro-2-hydroxy-propyl-trimethylammonium chloride crystallized out. The heterogeneous mixture was cooled to room temperature and filtered by means of suction. The crystals were washed twice, each time with 25 ml of ethanol/acetone 1:1 and dried. The yield was 17.65 g (93.6 percent) of (−)-3-chloro-2-hydroxy-propyltrimethylammonium chloride. Also, $[\alpha]_D^{24} = -29.8°$ (c=1.0 H$_2$O).

What is claimed is:

1. Optically-active di-[3-chloro-2-hydroxy-propyl-trimethylammonium]-tartrate.
2. Di-[(−)-3-chloro-2-hydroxy-propyltrimethylammonium]-L-(+)-tartrate.
3. Di-[(+)-3-chloro-2-hydroxy-propyltrimethylammonium]-D-(−)-tartrate.

* * * * *

UNITED STATES PATENT AND TRADEMARK OFFICE
CERTIFICATE OF CORRECTION

PATENT NO. : 4,670,192

DATED : June 2, 1987

INVENTOR(S) : Leander Tenud et al.

It is certified that error appears in the above-identified patent and that said Letters Patent is hereby corrected as shown below:

On the title page

-- [30] Foreign Application Priority Data should read

Apr. 4, 1984 [CH] Switzerland ......... 1704/84 --.

Signed and Sealed this

Sixteenth Day of February, 1988

Attest:

DONALD J. QUIGG

Attesting Officer

Commissioner of Patents and Trademarks